(12) United States Patent
Yasuda et al.

(10) Patent No.: US 9,939,375 B2
(45) Date of Patent: Apr. 10, 2018

(54) CONCENTRATION MEASUREMENT DEVICE

(71) Applicant: Murata Manufacturing Co., Ltd., Nagaokakyo, Kyoto-fu (JP)

(72) Inventors: Masaaki Yasuda, Nagaokakyo (JP); Masanori Tsubono, Nagaokakyo (JP); Naoki Ogushi, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 15/384,351

(22) Filed: Dec. 20, 2016

(65) Prior Publication Data

US 2017/0102325 A1 Apr. 13, 2017

Related U.S. Application Data

(63) Continuation of application No. PCT/JP2015/066872, filed on Jun. 11, 2015.

(30) Foreign Application Priority Data

Jul. 3, 2014 (JP) .................................. 2014-137786

(51) Int. Cl.
*G01J 5/00* (2006.01)
*G01N 21/3504* (2014.01)
(Continued)

(52) U.S. Cl.
CPC ......... *G01N 21/3504* (2013.01); *G01N 21/61* (2013.01); *G01N 33/004* (2013.01); *G01N 2201/0686* (2013.01)

(58) Field of Classification Search
CPC .................................................. G01N 21/3504
See application file for complete search history.

(56) References Cited

U.S. PATENT DOCUMENTS 5,463,433 A * 10/1995 Koo ...................... G03B 21/16
348/743
5,585,635 A 12/1996 Graham
(Continued)

FOREIGN PATENT DOCUMENTS

JP 5-203573 A 8/1993
JP 8-105833 A 4/1996
(Continued)

OTHER PUBLICATIONS

Official Communication issued in corresponding International Application PCT/JP2015/066872, dated Sep. 8, 2015.

*Primary Examiner* — Kiho Kim
(74) *Attorney, Agent, or Firm* — Keating & Bennett, LLP

(57) ABSTRACT

A gas concentration measurement device measures a gas concentration based on an absorbance of sample gas in a region between a light source that emits infrared light and a detector that detects the infrared light. The gas concentration measurement device includes a rotating member, first and second band pass filters on the rotating member, and a rotational driver. The first and second band pass filters are located on a pair of planes that intersect each other. The rotational driver rotates the rotating member around the rotating shaft to switch between a first state, in which the infrared light from the light source is transmitted through the first band pass filter, and a second state, in which the infrared light from the light source is transmitted through the second band pass filter.

15 Claims, 7 Drawing Sheets

(51) Int. Cl.
G01N 21/61 (2006.01)
G01N 33/00 (2006.01)

(56) References Cited

U.S. PATENT DOCUMENTS

| | | | |
|---|---|---|---|
| 2003/0063280 A1* | 4/2003 | Ando | G01J 3/02 |
| | | | 356/419 |
| 2010/0027004 A1 | 2/2010 | Bonyuet et al. | |
| 2010/0290045 A1 | 11/2010 | Saptari | |
| 2011/0090505 A1 | 4/2011 | Kuze et al. | |
| 2013/0119254 A1 | 5/2013 | Russell | |

FOREIGN PATENT DOCUMENTS

| | | | |
|---|---|---|---|
| JP | 2013-515963 A | | 5/2013 |
| KR | 2006085027 A | * | 7/2006 |
| WO | 2009/148134 A1 | | 12/2009 |

* cited by examiner

CONCENTRATION MEASUREMENT DEVICE

CROSS REFERENCE TO RELATED APPLICATIONS

This application claims the benefit of priority to Japanese Patent Application No. 2014-137786 filed on Jul. 3, 2014 and is a Continuation Application of PCT Application No. PCT/JP2015/066872 filed on Jun. 11, 2015. The entire contents of each application are hereby incorporated herein by reference.

BACKGROUND OF THE INVENTION

1. Field of the Invention

The present invention relates to an infrared-light-absorption gas concentration measurement device.

2. Description of the Related Art

A gas concentration measurement device that uses the non-dispersive infrared (NDIR) absorption method is an example of a known concentration measurement device for measuring the concentration of a specific component contained in sample gas or the like. This type of gas concentration measurement device causes sample gas to absorb infrared light emitted from a light source, and then detects the amount of infrared light that has passed through an optical filter (band pass filter) with a detector. The concentration of the sample gas is determined on the basis of the amount of light with a specific wavelength that has been absorbed.

Japanese Unexamined Patent Application Publication No. 5-203573, for example, discloses such a gas concentration measurement device. The gas concentration measurement device described in Japanese Unexamined Patent Application Publication No. 5-203573 is capable of measuring a plurality of types of sample gas by rotating a disc on which a plurality of band pass filters are arranged with intervals therebetween in a circumferential direction.

However, in the gas concentration measurement device disclosed in Japanese Unexamined Patent Application Publication No. 5-203573, the band pass filter to be used is switched by rotating the disc around a rotation axis that is parallel to the direction in which the band pass filter and the detector are arranged during the concentration measurement. The disc is large because the band pass filters are arranged in the circumferential direction on the disc. Accordingly, the gas concentration measurement device is required to have a rotation region in which the disc rotates, and is therefore also large. It is difficult to install such a large gas concentration measurement device in a small space.

SUMMARY OF THE INVENTION

Preferred embodiments of the present invention provide a gas concentration measurement device that is significantly reduced in size.

A gas concentration measurement device according to a preferred embodiment of the present invention measures a gas concentration based on an absorbance of sample gas in a region between a light source that emits infrared light and a detector that detects the infrared light. The gas concentration measurement device includes a rotating member that is rotatable around a predetermined rotating shaft; a first band pass filter and a second band pass filter provided on the rotating member; and a rotational driver that rotates the rotating member around the rotating shaft. The first band pass filter and the second band pass filter are located on a pair of planes that intersect each other. The rotational driver rotates the rotating member around the rotating shaft to switch between a first state, in which the infrared light from the light source is transmitted through the first band pass filter, and a second state, in which the infrared light from the light source is transmitted through the second band pass filter.

A gas concentration measurement device according to a preferred embodiment of the present invention measures a gas concentration based on an absorbance of sample gas in a region between a light source that emits infrared light and a detector that detects the infrared light. The gas concentration measurement device includes a rotating member that is rotatable around a predetermined rotating shaft; a first band pass filter and a second band pass filter provided on the rotating member; and a rotational driver that rotates the rotating member around the rotating shaft. The rotating shaft intersects an optical axis direction of the infrared light that travels from the light source toward the detector. The rotational driver rotates the rotating member around the rotating shaft to switch between a first state, in which the infrared light from the light source is transmitted through the first band pass filter, and a second state, in which the infrared light from the light source is transmitted through the second band pass filter.

In a gas concentration measurement device according to a preferred embodiment of the present invention, the first band pass filter is preferably a band pass filter that transmits the infrared light in an absorption band of the sample gas. In addition, the second band pass filter is preferably a band pass filter that blocks the infrared light in the absorption band of the sample gas and transmits the infrared light with a wavelength that is different from a wavelength of the infrared light transmitted by the first band pass filter.

In a gas concentration measurement devices according to a preferred embodiment of the present invention, preferably, the plane on which the first band pass filter is located and the plane on which the second band pass filter is located are perpendicular or substantially perpendicular to each other.

A gas concentration measurement device according to a preferred embodiment of the present invention preferably includes n band pass filters, n being an integer of 2 or more, that are provided on the rotating member and that include the first band pass filter and the second band pass filter. The n band pass filters are preferably located on n planes that intersect each other. A crossing angle between each of the n planes and another plane that is adjacent to each of the n planes is θ degrees, and Expression (1) is preferably satisfied:

$$[\{(n-1) \times 180\}/n] - 5 \leq \theta \leq [\{(n-1) \times 180\}/n] + 5 \qquad \text{Expression (1)}$$

In a gas concentration measurement device according to a preferred embodiment of the present invention, the rotational driver preferably includes a stepper motor.

Preferably, a gas concentration measurement devices according to a preferred embodiment of the present invention further include a housing. The housing preferably contains the rotational driver and a sample cell in which the rotating member is disposed.

According to various preferred embodiments of the present invention, gas concentration measurement devices that are significantly reduced in size are provided.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
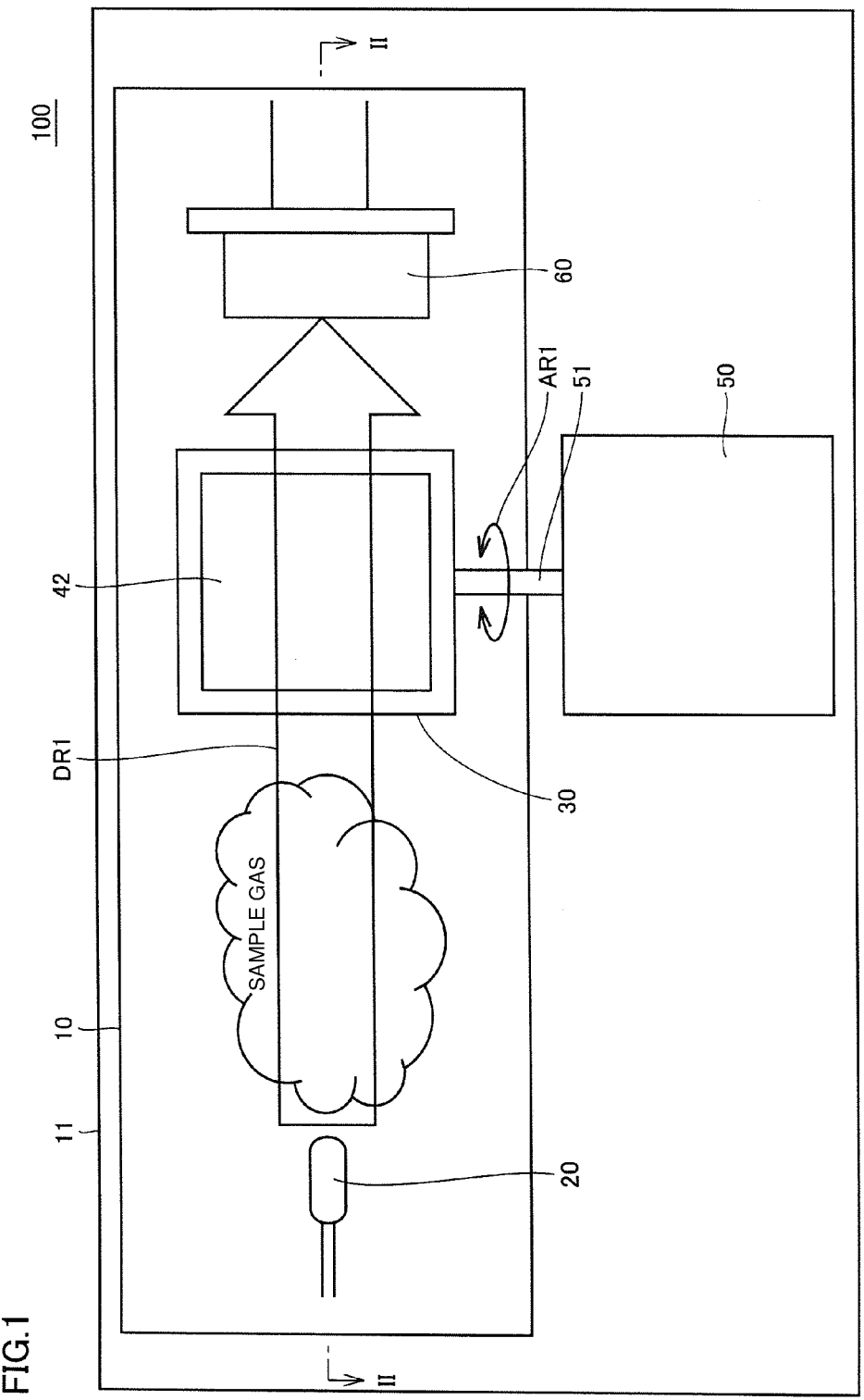
FIG. 1 is a top view of a gas concentration measurement device according to a first preferred embodiment of the present invention.

Preferred embodiments of the present invention will be described in detail with reference to the drawings. In the preferred embodiments described below, components that are the same or similar are denoted by the same reference numerals in the drawings, and descriptions thereof will not be repeated.

First Preferred Embodiment

Figure 2:
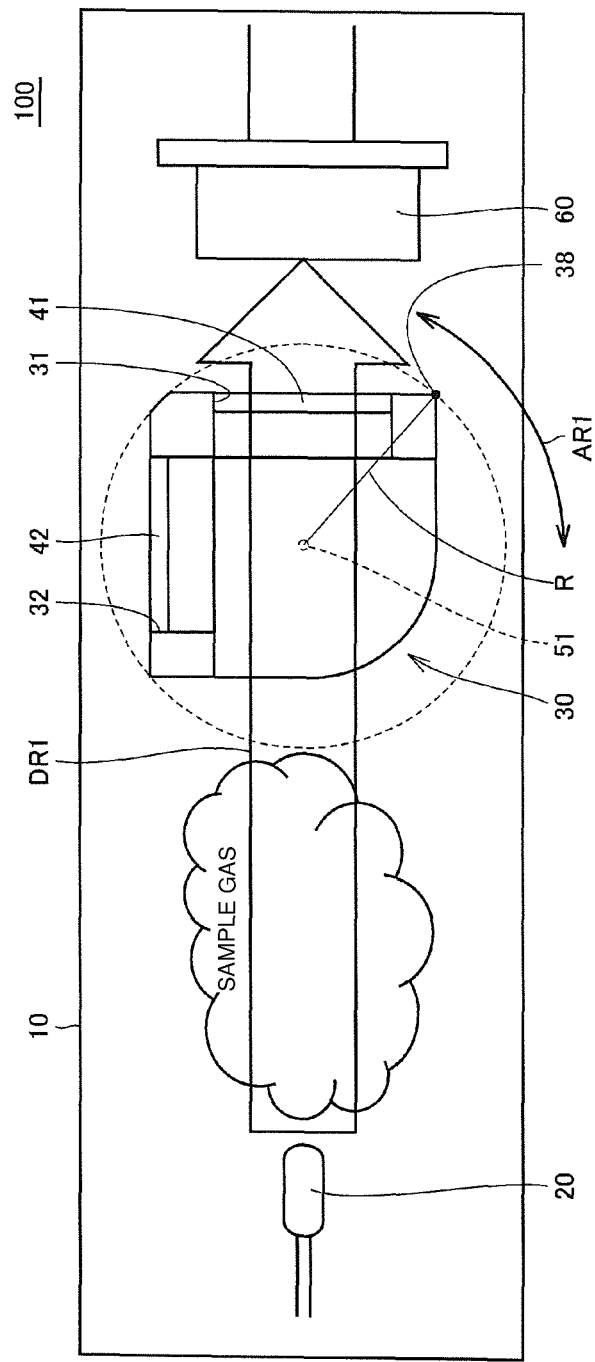
FIG. 2 is a sectional view taken along line II-II in FIG. 1, illustrating a first state of a rotating member.
Figure 3:
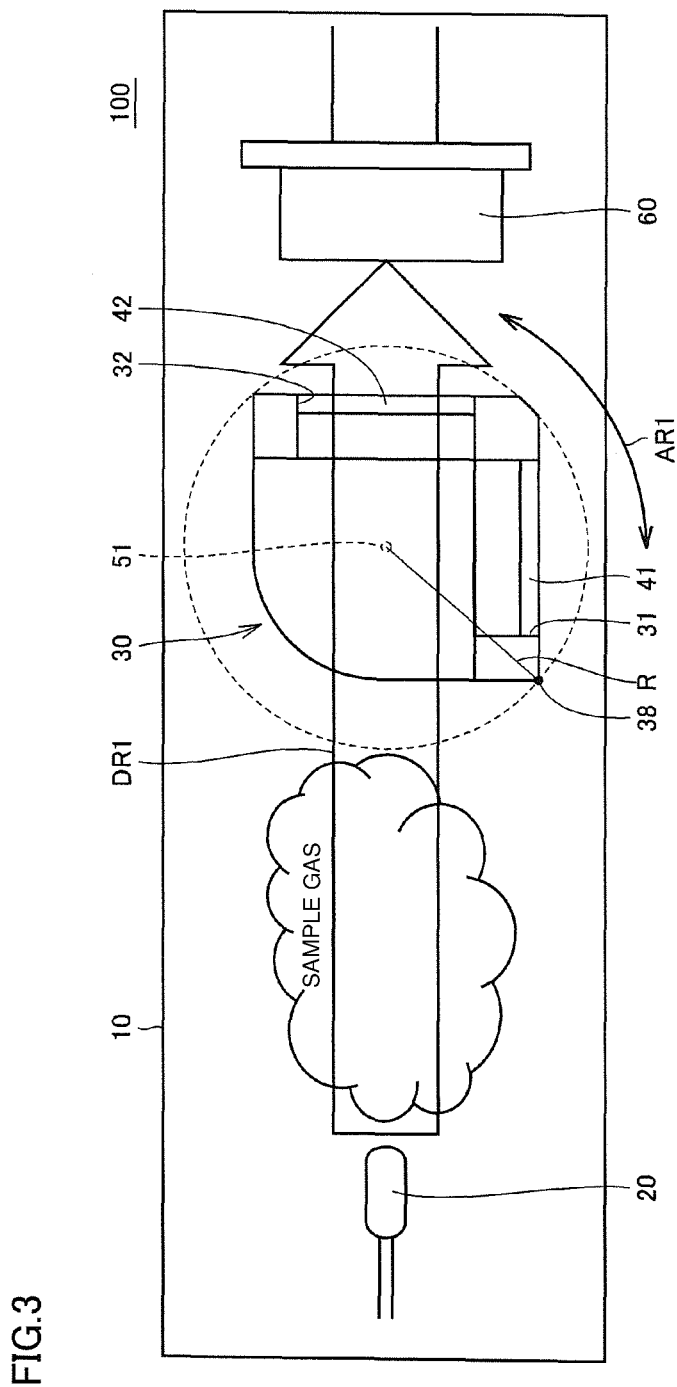
FIG. 3 is a sectional view taken along line II-II in FIG. 1, illustrating a second state of the rotating member.

FIG. 1 is a top view of a gas concentration measurement device according to the present preferred embodiment. FIG. 2 is a sectional view taken along line II-II in FIG. 1, illustrating a first state of a rotating member. FIG. 3 is a sectional view taken along line II-II in FIG. 1, illustrating a second state of the rotating member. A gas concentration measurement device 100 according to the present preferred embodiment will be described with reference to FIGS. 1 to 3.

As illustrated in FIGS. 1 to 3, the gas concentration measurement device 100 according to the present preferred embodiment includes a housing 11 containing a sample cell 10 and a rotational driver 50. The gas concentration measurement device 100 also includes the sample cell 10, a light source 20, a rotating holder 30, a first band pass filter 41 (see FIG. 2), a second band pass filter 42, and a detector 60. The rotating holder 30 corresponds to a "rotating member".

The gas concentration measurement device 100 measures a gas concentration in accordance with the absorbance of sample gas that flows through a space between the light source 20, which emits infrared light, and the detector 60, which includes a light-receiving portion 62 that receives the infrared light.

The sample cell 10 includes a sample-gas flow space and allows the sample gas to flow therethrough. For example, a sample-gas introduction hole (not shown) is connected to one end of the sample cell 10 (an end close to the light source 20 in FIG. 1), and a sample-gas discharge hole (not shown) is connected to the other end of the sample cell 10 (an end close to the detector 60 in FIG. 1). The sample gas introduced into the sample cell 10 through the sample-gas introduction hole is discharged through the sample-gas discharge hole.

The sample cell 10 contains the light source 20, the rotating holder 30, and the detector 60. The light source 20, the rotating holder 30, and the detector 60 are arranged, for example, in that order from one end of the sample cell 10. The rotational driver 50 is disposed outside the sample cell 10. The sample cell 10 is either an integral portion of the housing 11 or a separate and distinct structure from the housing 11.

The light source 20 emits infrared light. The light source 20 is, for example, a filament lamp or an LED lamp that emits wide-band infrared light including desired infrared light. A portion of the infrared light emitted from the light source 20 is absorbed depending on infrared light absorption wavelength characteristics of the sample gas. The infrared light emitted from the light source 20 mainly travels in an optical axis direction (the direction of arrow DR1 in the drawings) and reaches the detector 60.

The first band pass filter 41 and the second band pass filter 42 are provided on the rotating holder 30. More specifically, the first band pass filter 41 and the second band pass filter 42 are held by the rotating holder 30 in a region around a predetermined rotating shaft 51, which will be described below. The rotating holder 30 is rotated by the rotational driver 50 so that the first band pass filter 41 and the second band pass filter 42 are selectively disposed in a transmitting position, at which the infrared light emitted from the light source 20 is transmitted toward the detector 60.

The first band pass filter 41 transmits the infrared light in an absorption band of the sample gas to be detected. Thus, only the infrared light having a desired wavelength band reaches the detector 60. The sample gas to be detected is, for example, carbon dioxide, and the absorption band thereof is about 4.3 μm.

The second band pass filter 42 blocks the infrared light in the absorption band of the sample gas and transmits the infrared light with a wavelength that is different from that of the infrared light transmitted by the first band pass filter 41. The second band pass filter 42 transmits, for example, the infrared light in an approximately 3.9 μm band, which is not absorbed by the sample gas.

In general, it is known that the output of the detector 60 drifts due to variations in the amount of infrared light from the light source 20 and the ambient temperature. In the present preferred embodiment, the second band pass filter 42 (band pass filter for reference light) and the first band pass filter 41 are switched to calculate the amount of change in the value of wavelength of the absorption band of the sample gas with respect to the value of wavelength at which the sample gas is not absorbed, so that the detection sensitivity of the detector 60 is able to be corrected. Accordingly, the detection sensitivity of the detector 60 is constant or substantially constant.

The second band pass filter 42 may alternatively transmit the infrared light in an absorption band of another type of sample gas to be detected. In such a case, the concentrations of a plurality of types of sample gas are able to be measured.

The rotating holder 30 holds the first band pass filter 41 and the second band pass filter 42 in a first through hole 31 and a second through hole 32, respectively, and is rotatable around the rotating shaft 51 (in the direction denoted by AR1 in FIG. 1). The first through hole 31 and the second through hole 32 will be described below. The rotating holder 30 holds the first band pass filter 41 and the second band pass filter 42 so that the first band pass filter 41 and the second band pass filter 42 are located on planes 71 and 72 (see FIG. 5) that intersect each other. The rotating holder 30 includes a maximum radius portion 38 at which the radius of gyration R around the rotating shaft 51 is at a maximum. The inner diameter of the sample cell 10 is preferably greater than about twice the radius of gyration R to enable the rotation of the rotating holder 30. The rotating shaft 51 is parallel or substantially parallel to the pair of intersecting planes 71 and 72 on which the first band pass filter 41 and the second band pass filter 42 are located.

The rotational driver 50 is connected to the rotating holder 30 by the rotating shaft 51. The rotating shaft 51 extends through a hole (not shown) provided in a wall of the sample cell. Thus, the rotating shaft 51 connects the rotating holder 30, which is contained in the sample cell 10, and the rotational driver 50, which is disposed outside the sample cell 10.

The rotational driver 50 rotates the rotating holder 30 around the rotating shaft 51 to switch between the first state (see FIG. 2), in which the first band pass filter 41 is in the transmitting position, and the second state (see FIG. 3), in which the second band pass filter 42 is in the transmitting position.

The rotational driver 50 rotates the rotating holder 30 around the rotating shaft 51. When switching between the first state and the second state, the rotational driver 50 rotates the rotating holder 30 around the rotating shaft 51 by approximately 90 degrees, for example. The rotating shaft 51 intersects the optical axis direction DR1 of the infrared light. More specifically, the rotating shaft 51 is perpendicular or substantially perpendicular to the optical axis direction DR1 of the infrared light. Here, "substantially perpendicular" means that the crossing angle between the rotating shaft 51 and the optical axis direction DR1 of the infrared light is in the range of about 85 degrees to about 95 degrees, and a case in which the above-described crossing angle varies due to assembly is included.

The rotational driver 50 may be, for example, a stepper motor. When a stepper motor is used, the position repeatability of the rotating holder 30 is increased when switching between the first state and the second state. In addition, since the stepper motor exerts a holding torque without electricity, power consumption is significantly reduced.

The detector 60 may be an infrared light detector, such as a thermopile or a bolometer. The detector 60 is electrically connected to a signal processing circuit board (not shown). The detector 60 outputs an output signal to the signal processing circuit board based on the infrared light received by the light-receiving portion 62. The signal processing circuit board calculates the concentration of the sample gas based on the output signal of the detector 60.

Figure 4:
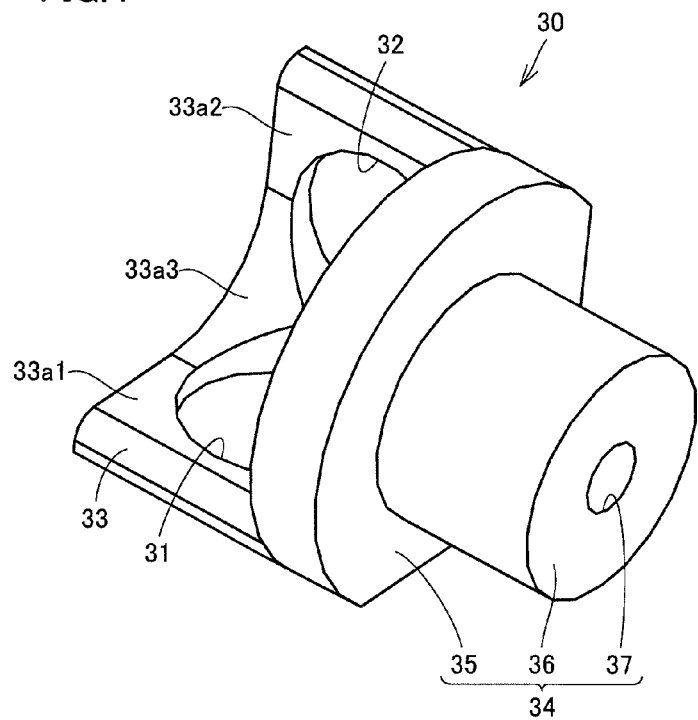
FIG. 4 is a schematic diagram of the rotating member illustrated in FIG. 1.
Figure 5:
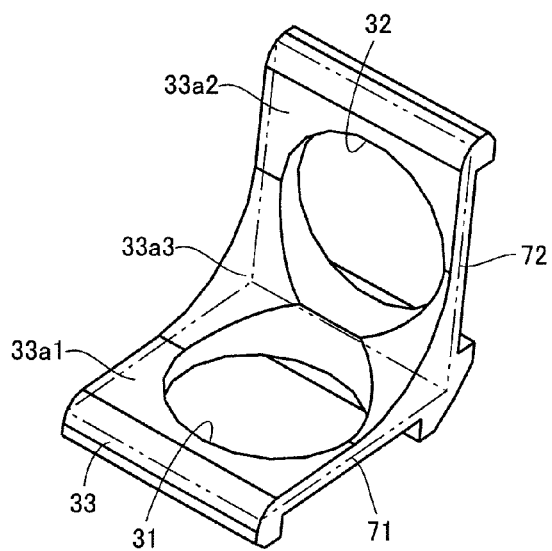
FIG. 5 is a schematic diagram of a main portion of the rotating member illustrated in FIG. 4.
Figure 6:
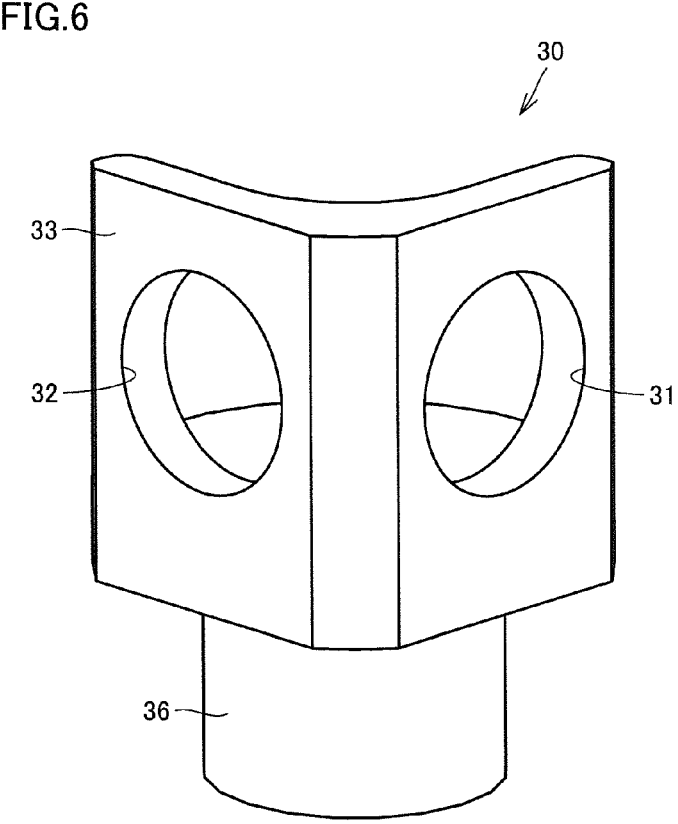
FIG. 6 is a schematic diagram illustrating outer side surfaces of the rotating member illustrated in FIG. 4.

FIG. 4 is a schematic diagram of the rotating member illustrated in FIG. 1. FIG. 5 is a schematic diagram of a main portion of the rotating member illustrated in FIG. 4. FIG. 6 is a schematic diagram illustrating outer side surfaces of the rotating member illustrated in FIG. 4. The detailed shape of the rotating holder 30 according to the present preferred embodiment will be described in detail with reference to FIGS. 4 to 6.

As illustrated in FIGS. 4 to 6, the rotating holder 30 includes a main portion 33 and a rotating shaft holder 34. The main portion 33 is L-shaped or substantially L-shaped. The main portion 33 is a portion that holds the first band pass filter 41 and the second band pass filter 42. The main portion 33 includes the first through hole 31, in which the first band pass filter 41 is securely fitted, and the second through hole 32, in which the second band pass filter 42 is securely fitted.

The inner peripheral surface of the main portion 33 includes a first flat portion 33a1, a second flat portion 33a2, and a connecting portion 33a3. The second flat portion 33a2 is flat and faces the detector 60 when the second band pass filter 42 is in the transmitting position.

The first flat portion 33a1 is flat and is parallel or substantially parallel to the axial direction of the rotating shaft 51 and the optical axis direction DR1 when the second band pass filter 42 is in the transmitting position. The first flat portion 33a1 is closer to the light source 20 than the second flat portion 33a2 when the second band pass filter 42 is in the transmitting position.

The connecting portion 33a3 connects the first flat portion 33a1 and the second flat portion 33a2 to each other. The connecting portion 33a3 is curved so as to approach the first flat portion 33a1 from the second flat portion 33a2 along the direction perpendicular or substantially perpendicular to the axial direction of the rotating shaft 51 and the optical axis direction DR1 when the second band pass filter 42 is in the transmitting position.

The first flat portion 33a1 and the second flat portion 33a2 are not necessarily flat, and alternatively may be warped to some extent. The connecting portion 33a3 is not necessarily curved, and may alternatively include, for example, a pair of flat surfaces that intersect at or substantially at, for example, a right angle.

When the second band pass filter 42 is in the transmitting position, the length of the main portion 33 in the optical axis direction DR1 is equal or substantially equal to the length of the main portion 33 in the direction perpendicular or substantially perpendicular to the axial direction of the rotating shaft 51 and the optical axis direction DR1.

The first band pass filter 41, is located in the first through hole 31 on the first plane 71. The second band pass filter is located in the second through hole 32 on the second plane 72. The first plane 71 and the second plane 72 are perpendicular or substantially perpendicular to each other. Here, "substantially perpendicular" means that the crossing angle θ between the first plane 71 and the second plane 72 is in the range of about 85 degrees to about 95 degrees, for example. Thus, a case in which the crossing angle between the first plane 71 and the second plane 72 differs from 90 degrees due to design errors is included.

The rotating shaft holder 34 includes a side wall portion and a rotating-shaft-receiving portion 36. The side wall portion 35 is, for example, fan-shaped or rectangular or substantially rectangular in plan view. The side wall portion 35 is provided at an end of the main portion 33 that is near the rotational driver 50.

The rotating-shaft-receiving portion 36 projects toward the rotational driver 50 in a direction normal to the outer principal surface of the side wall portion 35. The rotating-shaft-receiving portion 36 preferably is cylindrical or substantially cylindrical, and includes a receiving hole 37 that receives the rotating shaft 51. The rotating shaft 51 is inserted into the receiving hole 37 and fixed to the receiving hole 37 so that the rotating holder 30 rotates with the rotating shaft 51.

As described above, in the gas concentration measurement device 100 according to the present preferred embodiment, the rotating holder 30 holds the first band pass filter 41 and the second band pass filter 42 in such a manner that the first band pass filter 41 and the second band pass filter 42 are located on planes that intersect each other. Switching between the first state, in which the infrared light from the light source 20 is transmitted through the first band pass filter 41, and the second state, in which the infrared light from the light source 20 is transmitted through the second band pass filter 42, is performed by rotating the rotating holder 30 around the rotating shaft.

The rotating shaft 51 intersects the optical axis direction DR1 of the infrared light. Therefore, the area in which the rotating holder 30 rotates is smaller than the rotational area required when the rotating shaft is parallel to the optical axis direction of the infrared light as in the above-described Japanese Unexamined Patent Application Publication No. 5-203573. As a result, the size of the gas concentration measurement device 100 is significantly reduced.

Second Preferred Embodiment

Figure 7:
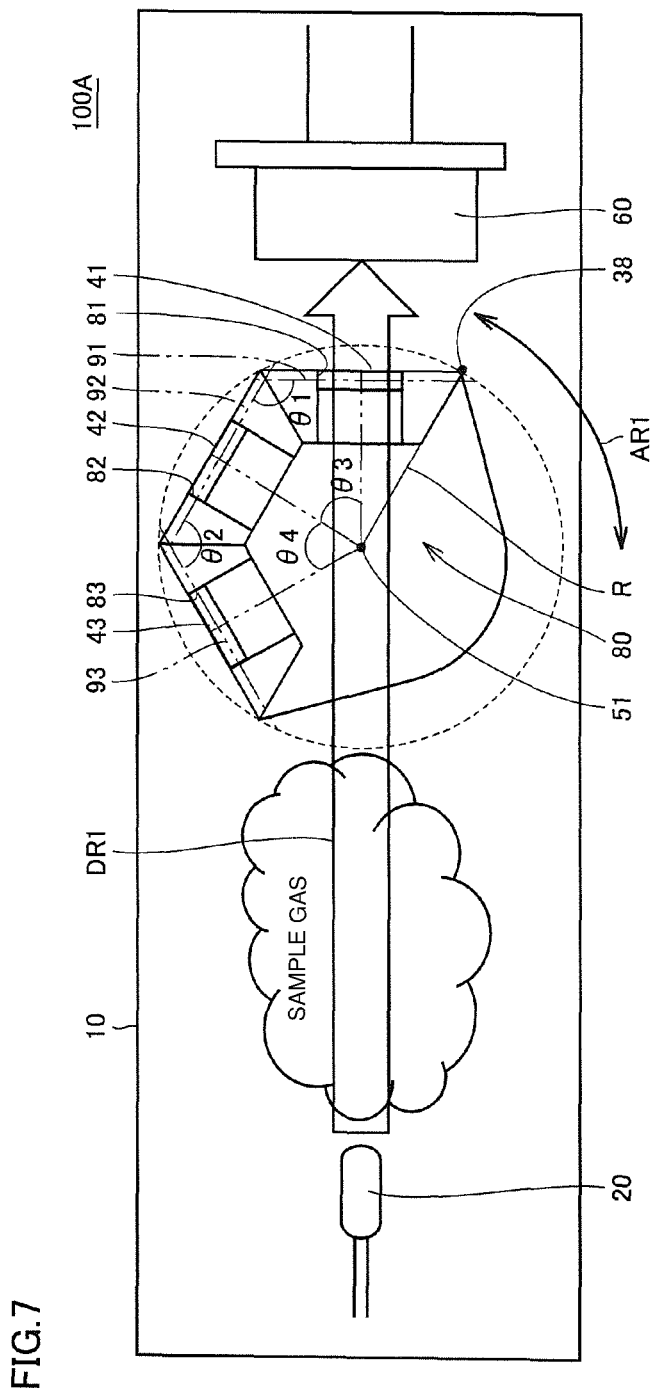
FIG. 7 is a sectional view of a gas concentration measurement device according to a second preferred embodiment of the present invention, illustrating a first state of the rotating member.
Figure 8:
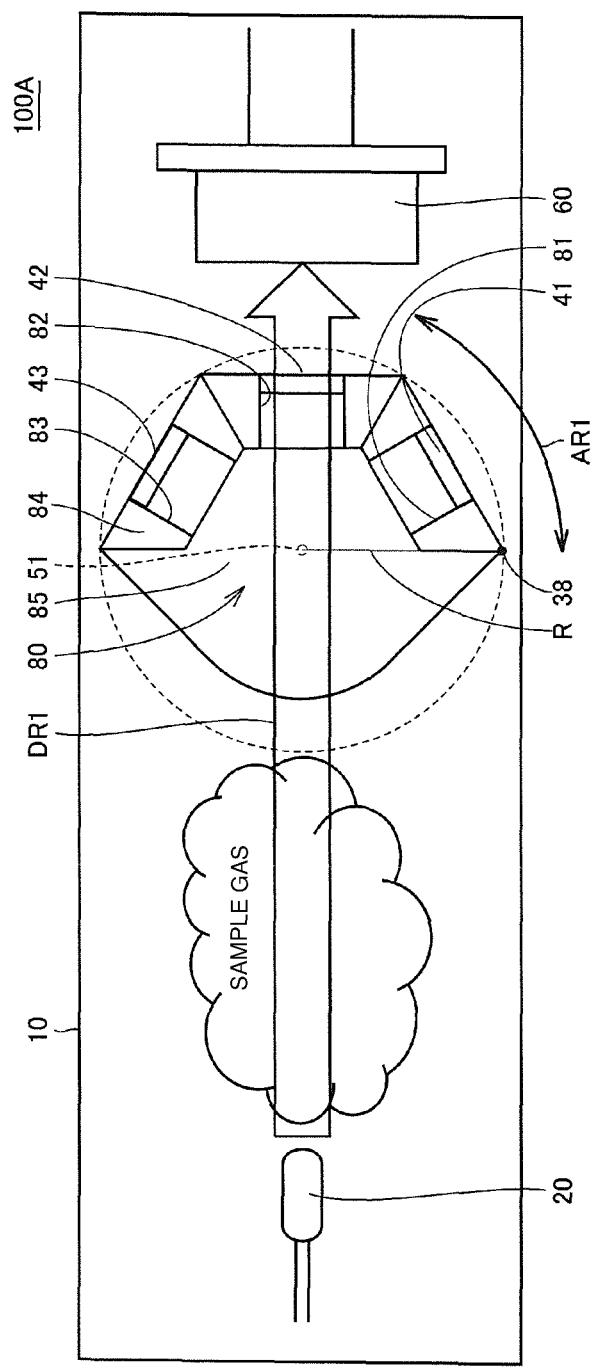
FIG. 8 is a sectional view of the gas concentration measurement device according to the second preferred embodiment of the present invention, illustrating a second state of the rotating member.

FIGS. 7 and 8 are sectional views of a gas concentration measurement device according to the present preferred embodiment, illustrating a first state and a second state, respectively, of a rotating member. The sectional views of FIGS. 7 and 8 correspond to the sectional views taken along line II-II in FIG. 1. A gas concentration measurement device 100A according to the present preferred embodiment will be described with reference to FIGS. 7 and 8.

Referring to FIGS. 7 and 8, in the gas concentration measurement device 100A according to the present preferred embodiment, the structure of a rotating member 80 and the number of band pass filters differ from those in the gas concentration measurement device 100 according to the first preferred embodiment. The other structures, such as the structure connecting the rotating member 80 to the rotational driver 50, of the present preferred embodiment are substantially the same as those of the first preferred embodiment.

The rotating member 80 holds a first band pass filter 41, a second band pass filter 42, and a third band pass filter 43, and is rotatable around the rotating shaft 51.

The first band pass filter 41 transmits the infrared light in an absorption band of the sample gas to be detected. Thus, only the infrared light with a desired wavelength band reaches the detector 60. The sample gas to be detected is, for example, carbon dioxide, and the absorption band thereof is about 4.3 μm.

The second band pass filter 42 transmits the infrared light with a wavelength that is different than that of the infrared light transmitted by the first band pass filter 41. The second band pass filter 42 transmits, for example, the infrared light in an approximately 3.9 μm band, which is not absorbed by the sample gas.

The third band pass filter 43 transmits the infrared light in an absorption band of another type of sample gas to be detected. Thus, only the infrared light with a desired wavelength band reaches the detector 60. The other type of sample gas to be detected is, for example, carbon dioxide, and the absorption band thereof is about 4.7 μm.

In the present preferred embodiment, the second band pass filter 42 (band pass filter for reference light), the first band pass filter 41, and the third band pass filter 43 (band pass filter that enables multiple measurements) are switched to calculate the amount of change in the value of wavelength of the absorption band of the sample gas with respect to the value of wavelength at which the sample gas is not absorbed, so that the detection sensitivity of the detector 60 is able to be corrected. Accordingly, the detection sensitivity of the detector 60 is constant or substantially constant, and the concentrations of a plurality of types of sample gas are able to be measured.

Although the other sample gas is carbon monoxide in the present preferred embodiment, the other sample gas is not so limited, and alternatively may be, for example, $CH_4$ or $NO_x$.

Although the first band pass filter 41, the second band pass filter 42, and the third band pass filter 43 are arranged in that order, the order of arrangement is not limited to this arrangement, and may be changed.

The rotating member 80 includes a main portion 84 including a first through hole 81 in which the first band pass filter 41 is securely fitted, a second through hole 82 in which the second band pass filter 42 is securely fitted, and a third through hole 83 in which the third band pass filter 43 is securely fitted.

The first band pass filter 41 is located on a first plane 91. The second band pass filter 42 is located on a second plane 92. The third band pass filter 43 is located on a third plane 93.

A crossing angle $\theta 1$ between the first plane 91 and the second plane 92 preferably is approximately 120 degrees, for example. A crossing angle $\theta 2$ between the second plane 92 and the third plane 93 preferably is approximately 120 degrees, for example. Here, an angle that is approximately 120 degrees is an angle in the range of 115 degrees to 125 degrees, for example. Thus, a case in which the crossing angles $\theta 1$ and $\theta 2$ vary due to design errors is included.

Thus, the peripheral shape of the main portion 84 of the rotating member 80 is preferably one-half of a regular hexagon when viewed in the rotation axis direction. The first through hole 81, the second through hole 82, and the third through hole 83 are arranged on respective side surfaces of the main portion 84. Therefore, when viewed in the rotation axis direction, the angle $\theta 3$ between the line that connects the rotation center and the center of the first band pass filter 41 and the line that connects the rotation center and the center of the second band pass filter 42 is approximately 60 degrees, and the angle $\theta 4$ between the line that connects the rotation center and the center of the second band pass filter 42 and the line that connects the rotation center and the center of the third band pass filter 43 is approximately 60 degrees, for example. Therefore, the band pass filter that is in the transmitting position is switched by rotating the rotating member 80 by approximately 60 degrees around the rotating shaft 51, for example.

When switching between a plurality of band pass filters such as band pass filters 41-43, the angle by which the rotating member 80 is rotated around the rotating shaft 51 is preferably set to an integer multiple of a feed angle corresponding to a single step of a stepper motor. When alternatively using a motor that is not a stepper motor, mechanical positioning may be performed by using a projection and an abutting-positioning portion, such as an abutting surface.

According to the above-described structure, also in the present preferred embodiment, the rotating shaft 51 intersects the optical axis direction DR1 of the infrared light. Therefore, similar to the first preferred embodiment, the size of the gas concentration measurement device 100A is significantly reduced. In addition, since a plurality of band pass filters are provided, the concentrations of a plurality of types of sample gas are able to be measured.

In the first and second preferred embodiments respectively described above, two band pass filters 41 and 42 are held by the rotating holder 30 and three band pass filters 41-43 are held by the rotating member 80. However, the number of band pass filters held by the rotating holder 30 and the rotating member 80 is not so limited, and may alternatively include four or more band pass filters, for example. In the second preferred embodiment, the peripheral shape of the main portion 84 of the rotating member 80 is preferably one-half of a regular polygon in which the number of sides is twice the number of band pass filters when viewed in the rotation axis direction. In the second preferred embodiment, preferably, first and second band pass filters 41 and 42 that are adjacent to each other are respectively located on first and second planes 91 and 92 that are different from each other, and the crossing angle θ1 between the first and second planes 91 and 92 is equal or substantially equal to the interior angle of the regular polygon.

More specifically, when n band pass filters are provided, n being an integer of 2 or more, the n band pass filters are arranged on n planes that intersect each other. When the crossing angle between adjacent planes of the n planes is θ degrees, Expression (1) is preferably satisfied. Expression (1) shows that the crossing angle θ varies in the range of about ±5 degrees due to design errors.

$$[\{(n-1)\times 180\}/n]-5 \leq \theta \leq [\{(n-1)\times 180\}/n]+5 \qquad \text{Expression (1)}.$$

Also when the above-described structure is used, the rotating shaft 51 intersects the optical axis direction DR1 of the infrared light. Therefore, similar to the above-described first and second preferred embodiments, the size of the gas concentration measurement device is significantly reduced. In addition, the concentrations of a plurality of types of sample gas are able to be measured.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A gas concentration measurement device that measures a gas concentration based on an absorbance of sample gas in a region between a light source that emits infrared light and a detector that detects the infrared light, the gas concentration measurement device comprising:
   a rotating member that is rotatable around a predetermined rotating shaft;
   n band pass filters including a first band pass filter and a second band pass filter provided on the rotating member, n being an integer equal to or greater than two; and
   a rotational driver that rotates the rotating member around the rotating shaft; wherein
   the first band pass filter and the second band pass filter are located on first and second planes that intersect each other;
   assuming that a polygon with 2*n vertexes surrounding the rotating shaft is defined, the n band pass filters are located on n planes along n continuous sides of the polygon;
   the rotational driver rotates the rotating member around the rotating shaft to switch between a first state, in which the infrared light from the light source is transmitted through the first band pass filter, and a second state, in which the infrared light from the light source is transmitted through the second band pass filter; and
   the rotating shaft is arranged so that a direction of the rotating shaft intersects the infrared light transmitting through the first band pass filter or the second band pass filter.

2. The gas concentration measurement device according to claim 1, wherein
   the first band pass filter is a band pass filter that transmits the infrared light in an absorption band of the sample gas; and
   the second band pass filter is a band pass filter that blocks the infrared light in the absorption band of the sample gas and transmits the infrared light with a wavelength different from a wavelength of the infrared light transmitted by the first band pass filter.

3. The gas concentration measurement device according to claim 1, wherein the first and second planes are perpendicular or substantially perpendicular to each other.

4. The gas concentration measurement device according to claim 1, wherein
   a number of crossing angles defined by the n continuous sides is n−1; and
   a crossing angle, of the number of crossing angles, between adjacent planes of the n planes is θ degrees and Expression (1) is satisfied:

$$[\{(n-1)\times 180\}/n]-5 \leq \theta \leq [\{(n-1)\times 180\}/n]+5 \qquad \text{Expression (1)}.$$

5. The gas concentration measurement device according to claim 1, wherein the rotational driver includes a stepper motor.

6. The gas concentration measurement device according to claim 1, further comprising:
   a housing that contains the rotational driver and a sample cell; wherein
   the rotating member is disposed in the sample cell.

7. The gas concentration measurement device according to claim 6, wherein the sample cell is an integral portion of the housing.

8. The gas concentration measurement device according to claim 6, wherein the sample cell and the housing are separate and distinct structures.

9. The gas concentration measurement device according to claim 6, wherein the rotational driver is disposed outside of the sample cell and inside of the housing.

10. The gas concentration measurement device according to claim 6, wherein the rotating shaft extends through a hole provided in a wall of the sample cell.

11. The gas concentration measurement device according to claim 1, wherein the rotating member includes a main portion that is L-shaped or substantially L-shaped.

12. The gas concentration measurement device according to claim 11, wherein the rotating member includes:
   a side wall portion that is connected to a surface of the main portion; and
   a rotating shaft receiving portion that is connected to the side wall portion and includes a receiving hole.

13. The gas concentration measurement device according to claim 1, wherein the rotating member includes holes in which the first band pass filter and the second band pass filter are fitted.

14. The gas concentration measurement device according to claim 1, wherein the rotational driver includes a motor that is not a stepper motor.

15. The gas concentration measurement device according to claim 1, wherein the rotating shaft extends perpendicular or substantially perpendicular to an optical axis direction of the infrared light that travels from the light source toward the detector.

* * * * *